(12) United States Patent
Pianowski et al.

(10) Patent No.: US 9,238,036 B2
(45) Date of Patent: Jan. 19, 2016

(54) PHARMACEUTICAL USES OF LANOSTA-8,24-DIEN-3-OLS

(75) Inventors: Luiz Francisco Pianowski, Mairiporá (BR); Joao Batista Calixto, Florianópolis (BR); Paulo Cesar Leal, Mairiporá (BR); Claudio Paulino Chaves, Fortaleza (BR)

(73) Assignee: AMAZONIA FITOMEDICAMENTOS LTDA, Fortaleza, CE (BR)

( * ) Notice: Subject to any disclaimer, the term of this patent is extended or adjusted under 35 U.S.C. 154(b) by 0 days.

(21) Appl. No.: 13/057,250

(22) PCT Filed: Aug. 5, 2008

(86) PCT No.: PCT/IB2008/002051
§ 371 (c)(1),
(2), (4) Date: Feb. 2, 2011

(87) PCT Pub. No.: WO2010/015874
PCT Pub. Date: Feb. 11, 2010

(65) Prior Publication Data
US 2011/0136773 A1 Jun. 9, 2011

(51) Int. Cl.
A61K 31/575 (2006.01)

(52) U.S. Cl.
CPC ................. *A61K 31/575* (2013.01)

(58) Field of Classification Search
CPC .................................................. A61K 31/575
USPC .......................... 552/544; 514/182
See application file for complete search history.

(56) References Cited

U.S. PATENT DOCUMENTS 3,625,954 A * 12/1971 Sarges .................. 548/309.4

FOREIGN PATENT DOCUMENTS

| FR | 2 617 | 6/1964 |
|---|---|---|
| WO | WO 03/041675 | 5/2003 |
| WO | WO 2006/007676 | 1/2006 |

OTHER PUBLICATIONS

Banno et al., Anti-inflammatory activities of the triterpene acids from the resin of Boswellia carteri. Journal of Ethnopharmacology, vol. 107, pp. 249-253, 2006.*
Zhang et al., Cancer-Related Neuropathic Pain: Mechanism and Therapy. Journal of Neuropathic Pain & Symptom Palliation, vol. 1(1), p. 55-67, 2005.*
Querfeld et al, "The Selective Protein Kinase C β Inhibitor Enzastaurin Induces Apoptosis in Cutaneous T-cell Lymphoma Cell Lines Through the AKT Pathway", 2006, pp. 1641-1647, vol. 126, Journal of Investigative Dermatology.
Graff et al, The Protein Kinase Cβ—Selective Inhibitor, Enzastaurin (LY317615.HCI), Suppresses Signaling Through The AKT Pathway, Induces Apoptosis, and Suppresses Growth of Human Colon Cancer and Giloblastoma Xenografts, Aug. 15, 2005, pp. 7462-7469, vol. 65, No. 16, Cancer Research.
Rizvi et al, "Enzastaurin (LY317615), A protein kinase Cβ inhibitor, inhibits the AKT pathway and induces apoptosis in multiple myeloma cell lines", Jul. 2006, pp. 1783-1789, vol. 5, No. 7, Mol. Cancer Ther.
International Search Report for PCT/IB2008/002051.
Yasukawa, Ken et al: "Inhibitory effect of euphol, a triterpene alcohol from the roots of Euphorbia kansui, on tumor promotion by 12-0-tetradecanoylphorbol-13-acetate in two-stage carcinogenesis in mouse skin", Journal of Pharmacy and Pharmacology, 52(1), 119-124, 1991.
Muzik, Frantisek: "Influence of lanosterol and chicken embryonal extract upon the course of 3,4-benzopyrene-induced skin carcinogenesis in mice", Ceskoslov. Onkol., 3, 313-22, 1956.
Yasukawa K et al: "Sterol and Triterpene Derivatives Form Plants Inhibit the Effects of a Tumor Promoter, and Sitosterol and Betulinic Acid Inhibit Tumor Formation in Mouse Skin Two-Stage Carcinogenesis", Oncology, S. Karger, Basel, CH, vol. 48, No. 1, (Jan. 1, 1991), pp. 72-76.

* cited by examiner

*Primary Examiner* — Barbara P Badio
(74) *Attorney, Agent, or Firm* — B. Aaron Schulman, Esq.; Stites & Harbison, PLLC.

(57) ABSTRACT

The invention generally refers to pharmaceutical uses of lanosta-8,24-dien-3-ols, a family of tetracyclic terpenols, as anti-inflammatory, anticancerigenous and analgesic agents via the inhibition of the disordered activation of serine-threonine protein kinases, particularly PKC.

4 Claims, 8 Drawing Sheets

PHARMACEUTICAL USES OF LANOSTA-8,24-DIEN-3-OLS

FIELD OF THE INVENTION

This invention generally refers to pharmaceutical uses of lanosta-8,24-dien-3-ols, a family of tetracyclic terpenols, as anti-inflammatory, anticancerigenous and/or analgesic agents via the inhibition of certain enzymes whose activity is linked to the proliferation of certain types of cancer.

In the text that follows, the compound euphol, a member of the lanosta-8,24-dien-3-ol family, will often be mentioned, and it is to be understood that this is done simply for ease of reference, and no other lanosta-8,24-dien-3-ol compound is, for this reason, excluded from the invention.

BACKGROUND OF THE INVENTION

Cancer is a name given to a group of more than 100 diseases which have in common the disorganized growth of cells that invade tissues and organs, and which may spread to other regions of the body, what is known as metastasis.

Different types of cancers correspond to the various types of body cells. For instance, there are several types of skin cancer, as the skin is formed by more than one type of cell. If the cancer starts in the epithelial tissues, such as skin or a mucosa, it is called carcinoma. If it starts in the conjunctive tissues, such as bone, muscle or cartilage, it is called sarcoma. Other characteristics that distinguish one cancer from the other are the cell multiplication speed, and their ability to invade other tissues and organs, close or far from its origin.

The type-C protein kinases (PKC) comprise a group of protein kinases whose function and regulation are highly conservative. Kinases are also called phosphotransferases, and they phosphorilate serine and threonine residues from their substrates and regulate various cell activities, including gene expression, mitosis, cell movement, metabolism and programmed cell death (apoptosis). PKC are subject to phosphorilation before being activated, such a process taking place during its translocation of cytosol to the plasmatic membrane. Their activation and cytosol translocation to the plasmatic membrane occur in response to the transitory increase of diacylglycerol (DAG), or to exogenous agents, known as phorbol esters, typically present in plants.

The PKC family comprises 12 isoforms, divided into three subcategories: conventional (cPKC, calcium-dependent, and activated by DAG and phosphatidylserine), original (nPKC, calcium-independent, but activated by DAG and phosphatidylserine), and atypical (aPKC, calcium-independent, and activated by phosphatidylserine, but not by DAG). Within a single cell, the isoforms present differences in their distribution, before and after the translocation to the cellular membrane, and the literature suggests that the function of each isoform associated to a certain cell may be conferred by differences in the subcellular location of the PKC in the eitoplasmatic compartments of membrane and nuclear.

In recent years several studies have shown a relation between the disordered activation of PKC and the development of pathological processes, including rheumatoid arthritis, multiple sclerosis, colitis and different types of cancer. The hypothesis about PKC involvement in cancer has received much attention lately, based specially on the findings that those enzymes are the substrate for natural promoters of tumors, the phorbol esters. The increased or reduced activation of the serine-threonine protein kinases, including PKC, or of the transcription factors modulated by them, may result in the disorganized growth of cells, inducing the cancer process. In that sense, many studies have shown that after the activation of the PKC there occurs an increase in the phosphorilation of transcription factors, among them the nuclear factor Kappa B (NF-κB) and the activator protein 1 (AP-1), which, by their turn, modulate the expression of several proteins important for the progression of tumors, including ciclooxigenase-2 (COX-2). In this way, the activation or blockage of such intracellular path ways, natural compounds can interfere in the growth and proliferation of abnormal cells.

Phorbol esters are derived from tetracyclic diterpenes and seem to be restricted to the Euphorbiaceae and Thymelaceae plant families. Such compounds are frequently studied due to their particular tumor-promoting inducement and pro-inflammatory actions. The molecular mechanisms that regulate the tumor-promoting inducement of phorbol esters are different from the mechanisms that trigger the inflammatory activity. The tumor-promoting inducement seems to be associated with their ability to replace DAG in the activation of PKC, and also to their capacity to stimulate the synthesis of the RNA and DNA proteins, behaving as mitogenic agents and stimulating cellular growth. As to the pro-inflammatory activity, phorbol esters mobilize phospholipids, liberate arachidonic acid and cause prostaglandin secretion, leading to inflammatory response of the tissues. The topical application of phorbol esters, particularly TPA (tetradecanoylphorbol-13-acetate), have contributed to the understanding of molecular mechanisms concerned with inflammatory processes and cancer.

Some PKC inhibitors have been tested for the treatment of cancer in different phases of pre-clinical tests. One of them is the enzastaurin (LY317615), which shows an important activity when administered orally, and efficacy in different models of cancer, in vitro and in vivo (Journal of Investigative Dermatology (2006) 126, 1641-1647; Cancer Res (2005) 65:7462-7469; Mol Cancer Ther. (2006) 5:1783-1789).

The main problem in the treatment of anti-inflammatory diseases with NSAID (non-steroidal anti-inflammatory drugs) and steroidal drugs (corticoids) is the adverse effects caused by them and their non total efficacy. The most frequently reported side effects are: headache, stomachache, vomits, diarrhea, gastropathies such as stomach and duodenum ulcers. Corticoids may raise blood pressure, cause asteny and myopathy, peptic ulcers, petechies, erythema, acne, chronic headache, hirsutism, growth suppression in children (in long treatments), amenorrhea, cataract and glaucoma, appetite and weight gain, nausea. NSAIDs, the selective of COX-2, also can increase risks of serious thrombotic cardiovascular events, coronary thrombosis, and strokes.

As to the effective treatment of cancer, the difficulty is to establish the distinction between malignant and normal body cells. They share the same origin and are very similar, leading to the lack of recognition on the part of the immunologic system faced with a threat. Up to now, cancer has been treated by way of surgery, chemotherapy, radiotherapy and immunotherapy (monoclonal antibody therapy). The choice of treatment depends on the location, degree of the tumor and phase of the disease, as well as the general state of the patient. The complete removal of the tumor, with no damage to the rest of the organism is the main objective of the treatment, which can sometimes be obtained by surgery, but the propensity of the disease to invade adjacent tissues or to propagate to distant sites (metastasis) often limits its efficacy. The efficacy of chemotherapy is often limited by the toxicity to other cells of the organism, whereas radiotherapy may damage normal tissue. In immunotherapy cancer cells develop mechanisms to escape the immunologic response, a phenomenon known as treatment resistance.

DETAILED DESCRIPTION OF THE INVENTION

Figure 1:
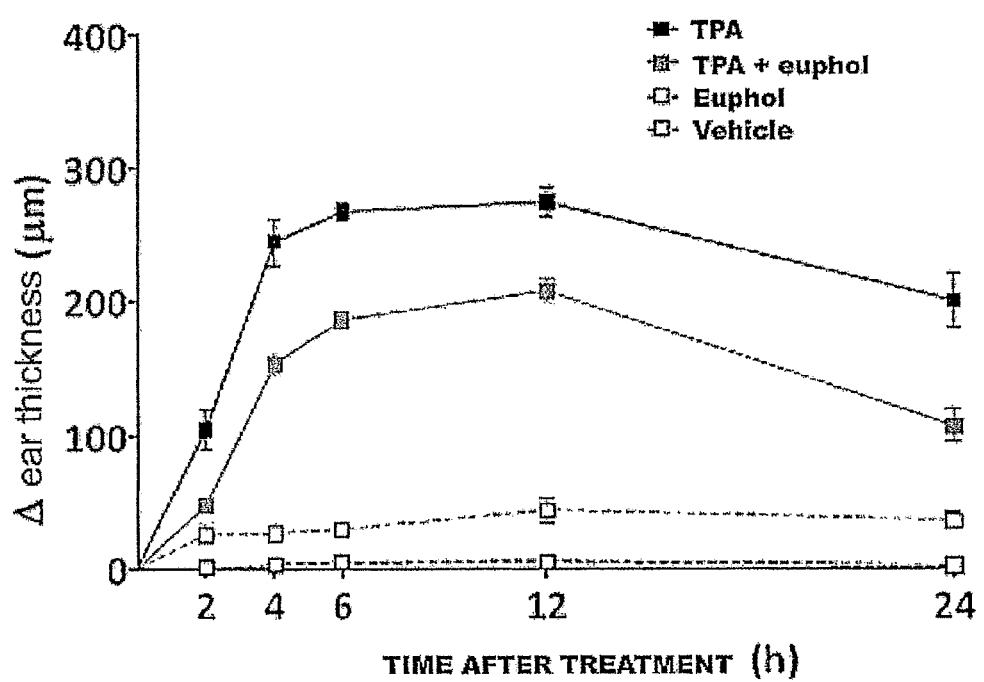
FIG. 1 shows the difference between the ear thickness before and after the application of the tested compounds, along time.

In view of the prior art, the present invention provides the use of lanosta-8,24-dien-3-ols for the inhibition of enzymes whose activity is linked to the proliferation of cancer cells, particularly PKC. Therefore, the invention also concerns lanosta-8,24-dien-3-ols for use in the effective treatment of tumors, inflammation and/or pain, significantly without the drawbacks known up to now.

Adequate lanosta-8,24-dien-3-ols are euphol, tirucallol and lanosterol, their isomers, derivatives (particularly acetates), solvates or hydrates, without excluding any other. Lanosta-8,24-dien-3-ols can be obtained for instance from Euphorbiaceae plants, or by chemical synthesis, the path being irrelevant to the invention.

Therefore, in a first aspect, the invention concerns the use of lanosta-8,24-dien-3-ols for the production of pharmaceutical compositions that inhibit the increased or reduced activation of serine-threonine protein kinases, or of the transcription factors modulated by them. The chemical compounds of the invention inhibit the activation of such kinases, particularly PKC (protein kinases C), whose activity is known to be linked to cancer cells. Also particularly, the transcription factors modulated by said kinases comprise the nuclear factor Kappa B (NF-κB) and/or the activator protein 1 (AP-1).

The lanosta-8,24-dien-3-ols of the invention, as well as compositions comprising them, can be administered to the subject in need of treatment in any adequate way, enteral or parenteral, including oral, topical, transdermal, subcutaneous, intraperitonial, intravenous, by infiltration, by inhalation, transdermal, transmucosal, intramuscular, intrapulmonary, vaginal, rectal, intraocular, and sublingual. Particularly adequate ways of administration in the present invention are topically and systemically (infiltration, oral, inhalation by spray, transdermal). The lanosta-8,24-dien-3-ols of the invention can be comprised in slow or controlled release compositions. Known adjuvants and excipients can be utilized in such compositions—a reference for pharmaceutical administration forms useful for the compositions related to the invention can be found in the publication Remington's Pharmaceutical Sciences, Mack Publishing, 1965-1990.

Without excluding any other compounds of the family, appropriate lanosta-8,24-dien-3-ols are one or more of euphol (RN 514-47-6), tirucallol (RN 514-46-5) and lanosterol (RN 79-63-0), more particularly euphol.

In another aspect, the invention concerns the use of lanosta-8,24-dien-3-ols, or compositions therewith, for the production of pharmaceutical compositions for the treatment of tumors and/or inflammation and/or pain (nociceptive responses).

The compositions of the invention can be administered to patients as solids, liquids or semi-liquids, tablets, capsules, pills, powder, granules, suspensions, emulsions, dispersions and any other useful known pharmaceutically acceptable form. The compositions might contain further active agents, for instance antibiotics, depending on the desired effect. For oral administration as tablets or capsules (both soft and hard capsules), the lanosta-8,24-dien-3-ols can be combined with pharmaceutically acceptable inert vehicles, such as lactose, starch, sucrose, glucose, methyl cellulose, magnesium stearate, dicalcium phosphate, calcium phosphate, manitol, sorbitol, and similars; for oral administration in the liquid form, the lanosta-8,24-dien-3-ols can be combined with ethanol, glycerol, water, and similars. When desired or necessary, agglomerating agents, lubricant agents, disintegrating agents, color and fragrance can be added to the mixture. Common agglomerating agents are glucose, [beta]-lactose, corn sweeteners, natural or synthetic gums such as gum arabica, tragacanth or sodium alginate, carboxymethylcellulose, polyethylene glycol, wax and similars. Lubricants include sodium oleate, sodium stearate, magnesium stearate, sodium benzoate, sodium acetate, sodium chloride. Disintegrants include starch, methyl cellulose, agar, bentonite, xanthan gum, and similars.

The compositions of the invention can also be administrated as liposomes or coupled with soluble polymers as vehicles.

Liquid dosage forms for oral administration may comprise colorants and edulcorants to increase acceptance by patients. Acceptable vehicles for water dosage forms are, water, an appropriate oil, a saline solution, aqueous dextrose, other sugar solutions and glycols as propylene glycol or polyethylene glycols, phosphate buffer.

In still another aspect, the invention concerns a method of medical treatment for bodily conditions of mammals linked to the disordered activation of serine-threonine protein kinases, more particularly PKC, when they influence the appearance or presence of inflammation and/or cancer and/or pain, said method comprising the administration to said mammal of a pharmacological effective amount for treatment of said condition in a pharmacologically acceptable carrier or excipient.

EXAMPLES

Though the following examples are concrete embodiments of the invention, they do not in any way impose limitations to it other than what is expressed in the claims presented further on.

In all examples that follow, 20-30 g male mice were kept in filtered-air ventilated cages, with controlled temperature (22±2° C.) and humidity (50-60%), 12 h light/12 h dark cycles, with free access to water and food. The animals remained in the lab for an adaptation period of at least 1 hour before the pharmacological tests, held between 8:00 and 17:00 h.

In all examples that follow, statistical analyses with the Graph Pad PRISM® 5.0 curve-fitting software were run.

Example 1

A characterization of the irritating effect of certain chemical compounds was effected, by comparing the results of treating mice ears topically with:
- a positive control, namely TPA (tetradecanoylphorbol-13-acetate), 2.5 µg/ear, in a vehicle comprising a 3:1 mixture of acetone:ethanol.
- a negative control, namely the vehicle, which is a 3:1 mixture of acetone:ethanol;
- Euphol, 100 µg/ear, a compound of the invention, in a vehicle comprising a 3:1 mixture of acetone:ethanol;
- A mixture of 100 µg of euphol and 2.5 µg TPA, per ear, in a vehicle comprising a 3:1 mixture of acetone:ethanol.

5-member groups of mice were topically applied, in the inner surface of the ears, the compositions above. The thickness of the ears, before and after exposure to the tested compositions, was measured using a digital micrometer, and the responses were expressed as mµ. FIG. 1 shows the difference between the ear thickness before and after the application of the tested compounds, along time.

The results are shown in FIG. 1.

As can be seen, the inhibitory effect obtained with euphol was significant even up to 24 hours after the treatment, indicating the important pharmacokinetic effect upon inflammation.

Example 2

This was an evaluation of the effect of the compounds of the invention upon the PKC activity, on the skin of mice. The animals received the following 100 µg/ear compositions:
- a positive control, namely TPA (tetradecanoylphorbol-13-acetate), 2.5 µg/ear, in a vehicle comprising a 3:1 mixture of acetone:ethanol.
- a negative control, namely the vehicle, which is a 3:1 mixture of acetone:ethanol;
- A mixture of 100 µg euphol and 2.5 µg TPA, per ear, in a vehicle comprising a 3:1 mixture of acetone:ethanol.

Figure 2:
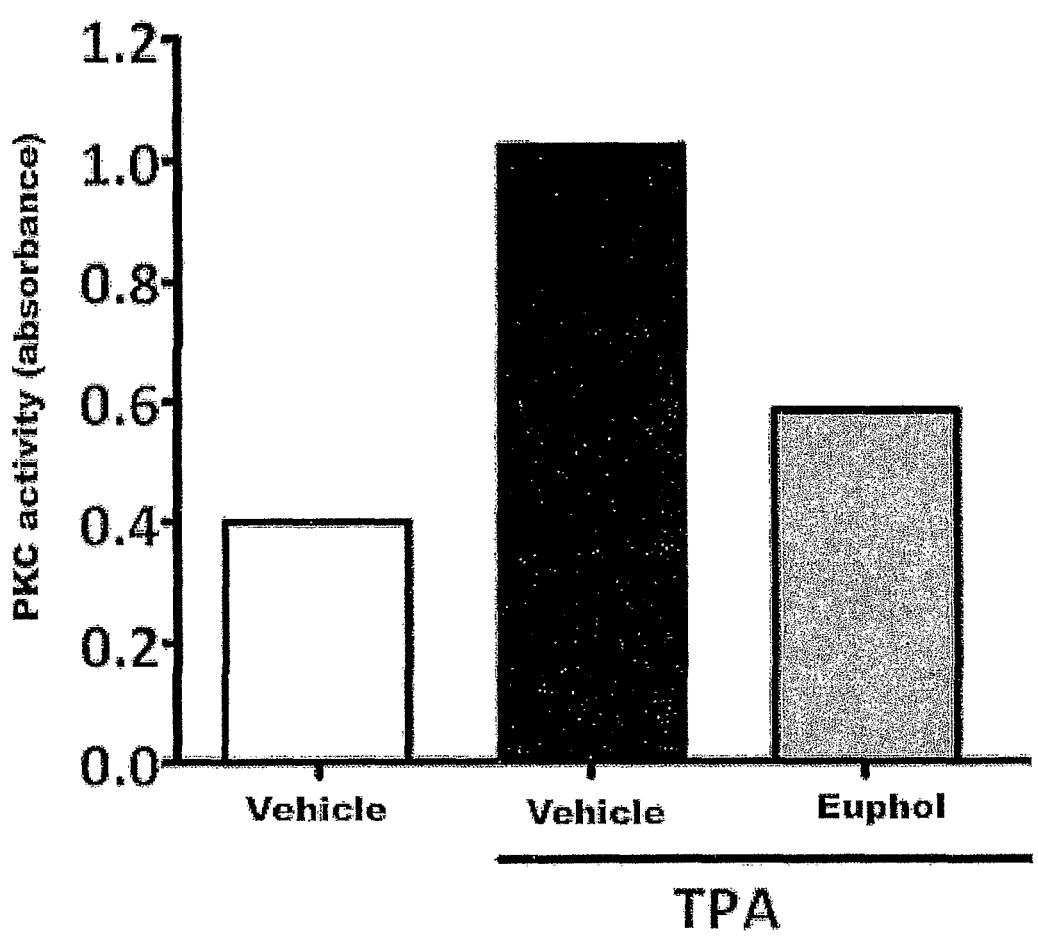
FIG. 2 shows the absorbance for the three tested compositions. White box: a positive control, namely TPA (tetradecanoylphorbol-13-acetate), 2.5 µg/ear, in a vehicle comprising a 3:1 mixture of acetone:ethanol; Black box: a negative control, namely the vehicle, which is a 3:1 mixture of acetone:ethanol; and Grey box: A mixture of 100 µg euphol and 2.5 µg TPA, per ear, in a vehicle comprising a 3:1 mixture of acetone:ethanol.

5-member groups of mice were topically applied, in the inner surface of the ears, the compositions above. The PKC activity, before and after exposure to the tested compositions, was measured using ELISA (enzyme-linked immuno sorbent assay). FIG. 2 shows the absorbance for the three tested compositions, mentioned above.

As can be seen, TPA promotes a significant increase in the PKC activity with respect to the group treated with the vehicle, whereas the treatment with euphol significantly reduces the increase in PKC activity induced by TPA.

Examples 3, 4 and 5

Nociception

The animals' nociceptive mechanical threshold was evaluated as the response frequency of paw withdrawal after ten applications of a Von Frey filament (VHF, Stoelting, Chicago, USA). The animals were individually placed in 9×7×11 cm transparent acrylic compartments over an elevated wire mesh platform, to allow access to the paw plantar surfaces. The Von Frey filament was applied to the right hind paw, watching the criteria of (1) application perpendicular to the plantar surface with enough pressure to bend the filament, so as to ensure total pressure; (2) the animals were evaluated when all four paws were accommodated on the wire mesh; (3) a paw withdrawal response was considered when the animal removed the paw entirely from the wire mesh; (4) each animal was stimulated 10 consecutive times, with 1 second duration each stimulation; (5) each paw withdrawal was considered as 10% of a response, with 10 withdrawals corresponding to 100% response.

Example 3

Inflammatory Nociception Induced by Carragenan

For the inducement of inflammatory pain, each animals received a 20 µl intraplantar carragenan injection (300 µg/paw) in the right hind paw. Animals treated with a 0.9% (20 µl/paw) PBS (phosphates buffered saline) solution were used as control. That carragenan dosage produces edema, nociception and significant size increase in the injected paw.

The animals were treated orally with euphol (30 µg/kg) one hour before the carragenan injection. Animals treated with subcutaneous injections of 0.5 mg/kg dexamethasone 4 hours before the carragenan injection were used as positive control. Hypernociception was evaluated hourly during 8 hours with a 0.6 g Von Frey filament, as well as after 24 and 48 hours after carragenan injection.

Figure 3A:
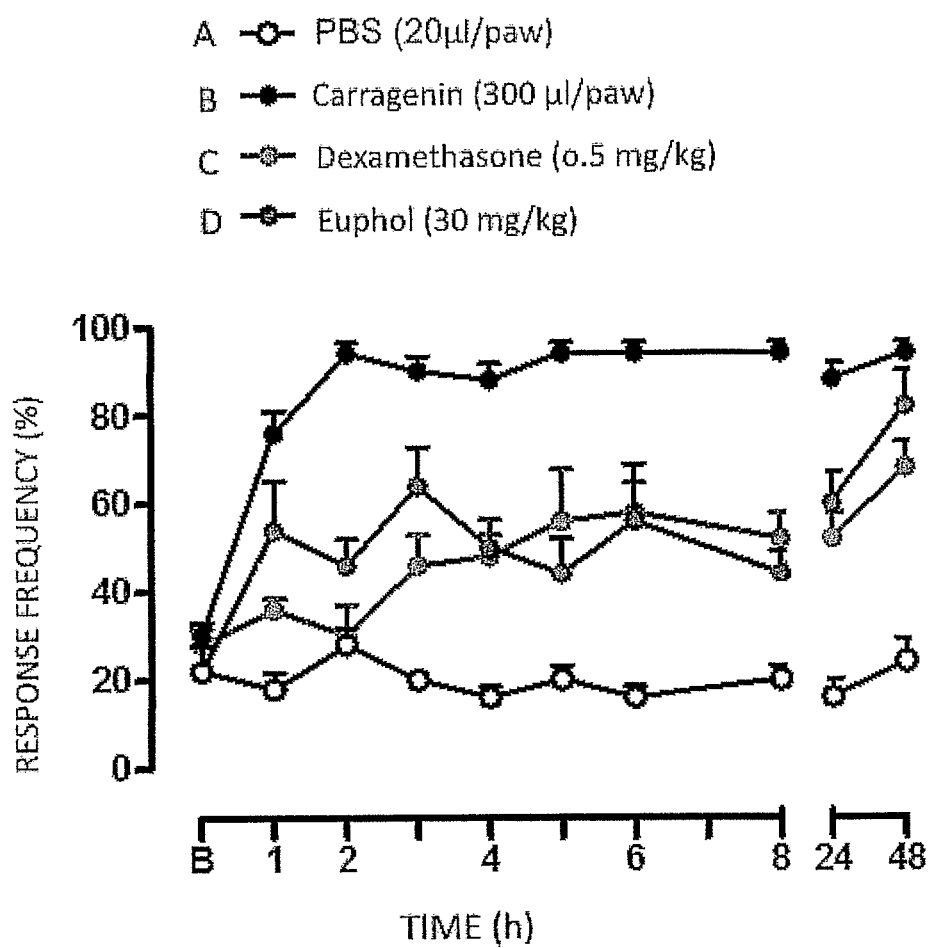
FIGS. 3A and 3B, 3A being a graph of time vs. frequency of response, and 3B the expression of the area under the curve of 3A for each tested compound, allowing a percentage comparison among them.
Figure 3B:
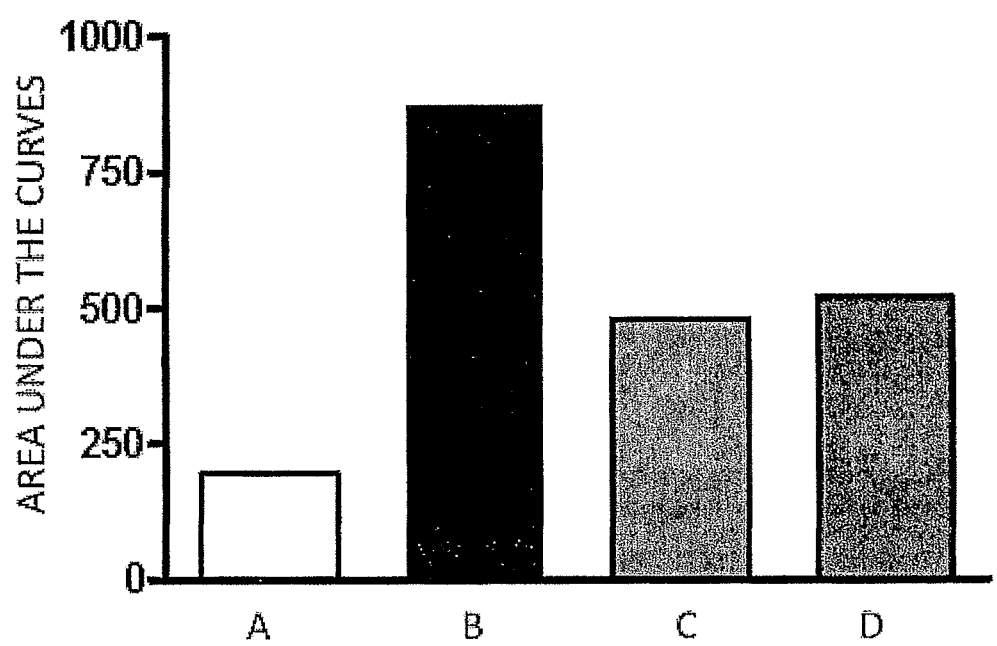

The results are shown in FIGS. 3A and 3B, 3A being a graph of time vs. frequency of response, and 3B the expression of the area under the curve of 3A for each tested compound, allowing a percentage comparison among them.

As can be seen in those figures, the acute treatment with euphol significantly reduced the inflammatory mechanical hypernociception induced by carragenan. Euphol lead to a reduction of nociceptive response similar to the control group treated with dexamethasone.

Example 4

Persistent Inflammatory Nociception Induced by CFA (Complete Freund's Adjuvant)

The animals were intraplantarly injected 25 µl CFA, a dose that produces hypernociception and increase in the size of the injected paw (*Neuropharmacology*, 41:1006-1012, 2001; *Anesth Analg.*, 101:1763-1769, 2005).

Animals were treated orally with 30 mg/kg euphol or 70 mg/kg gabapentin (positive control), 1 hour before the CFA injection. The mechanical hypernociception was measured through stimulation with a 0.6 g Von Frey filament in time intervals of 1, 2, 4, 6, 8, 24 and 48 hours after CFA injection, and up to the re-establishment of the nociceptive response. After that—$3^{rd}$ day—a chronic treatment was started to evaluate the prolonged treatment with euphol. For that, animals received daily 30 mg/kg euphol, orally, for 5 days, and hypernociception was evaluated once a day, 4 hours after the first administration. Mechanical hypernociception was evaluated until the return of the painful response. After that, the once-a-day treatment started again, for 5 days, to evaluate the development of tolerance for the compound, and hypernociception was evaluated up to the return of the nociceptive response.

Figure 4A:
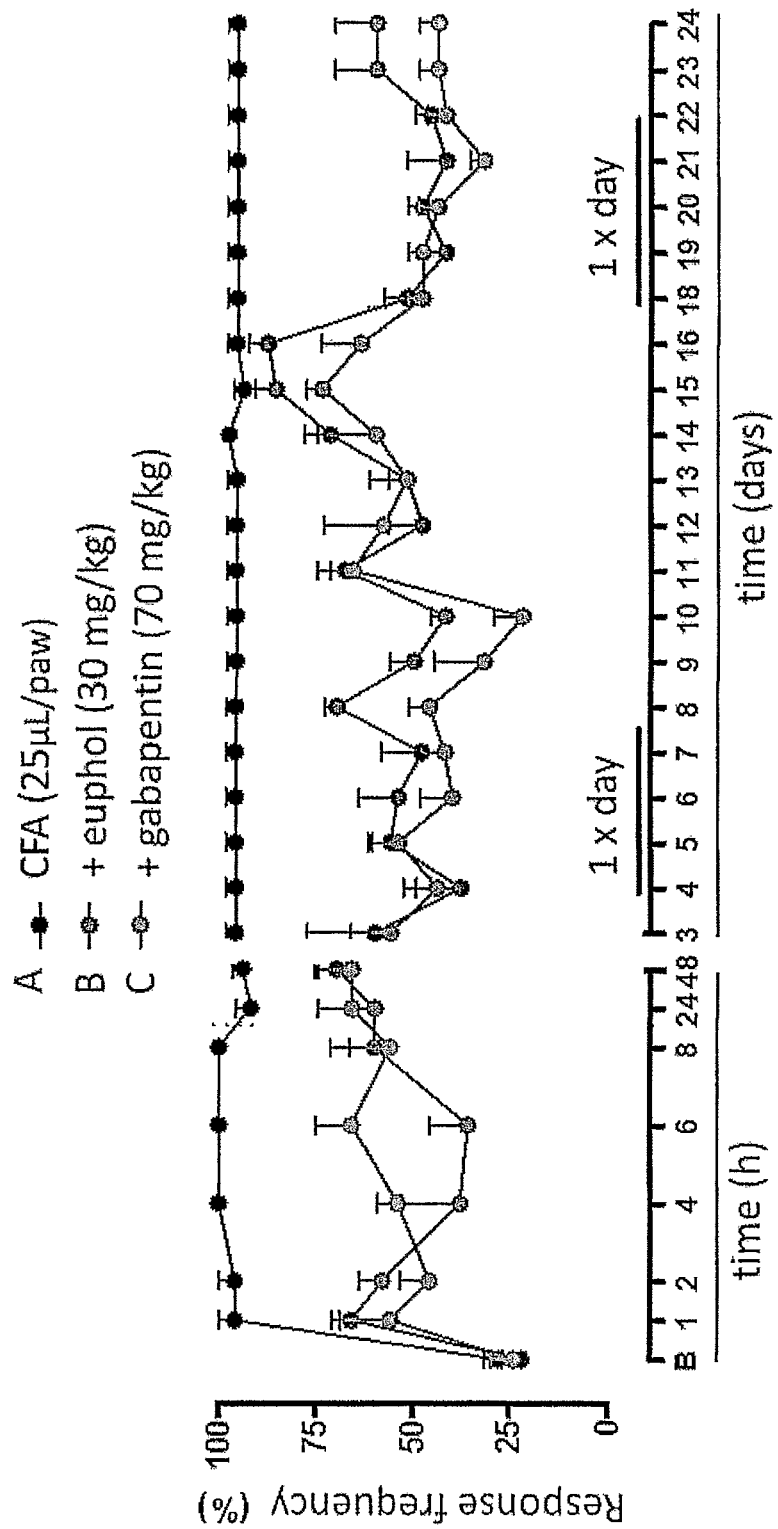
FIGS. 4A, 4B and 4C, 4A being a graph of time vs. frequency of response, and 4B and 4C the expression of the area under the curves of 4A for each tested compound, allowing a percentage comparison among them.
Figure 4B:
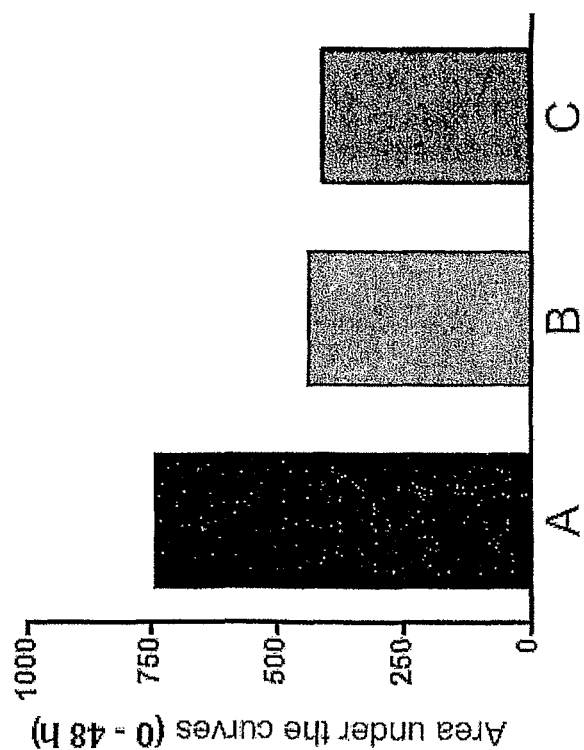
Figure 4C:
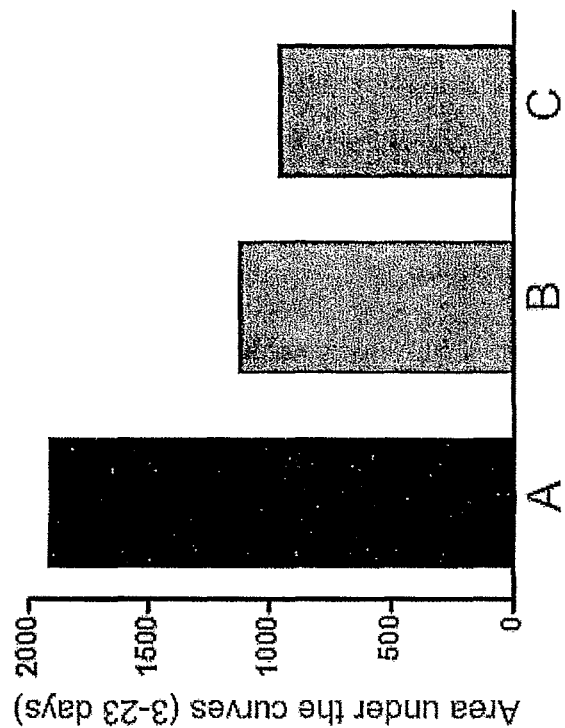

The results are shown in FIGS. 4A, 4B and 4C, 4A being a graph of time vs. frequency of response, and 4B and 4C the expression of the area under the curves of 4A for each tested compound, allowing a percentage comparison among them.

As can be seen in FIGS. 4A and 4B, the acute treatment with euphol reduced significantly the mechanical hypernociception induced by CFA, close to the effect obtained with gabapentin.

When euphol was administered once a day for 5 days, one observes the inhibition of the nociceptive response caused by CFA during the 6 following days of treatment. The mechanical hypernociception was reduced again with the start of the prolonged treatment, as seen with the aid of curves from the $3^{rd}$ to the $24^{th}$ day after the injection of CFA. Similar inhibition was observed with prolonged treatment with gabapentin.

Example 5

Neuropathic Pain Induced by Partial Constriction of the Sciatic Nerve

The procedure here employed was similar to the one described for rats (*Pain,* 43:205-218, 1990), modified for mice ((*Pain,* 76:215-222, 1998), and standardized by Bortolanza et al (*Eur J Pharmacol.,* 453:203-208, 2002). The mice were anesthetized with 7% chloral hydrate (0.6% ml/kg intraplantar). Then the sciatic nerve was exposed on top of the thigh about the sciatic trifurcation, and ⅓-½ of the dorsal portion was tied with a suture filament no. 8. In the false-operated group, the sciatic nerve was exposed without the tying. On the $4^{th}$ post-operatory day, a group of animals was treated orally with 30 mg/kg euphol, and another group treated orally with 70 mg/kg gabapentin, as a positive control. In predetermined times after the treatment (1, 2, 4, 6, 8, 24 and 48 hours) the mechanical threshold was evaluated, through stimulation with a 0.6 Von Frey filament. To assess the effect of the prolonged treatment, the animals were daily administered euphol, from the $6^{th}$ day, for 5 days and the mechanical hypernociception was evaluated once a day, 4 h after the first administration, until the return of the nociceptive response similar to the control group. After that, the prolonged treatment protocol was repeated to evaluate a possible development of tolerance to the compound.

Figure 5A:
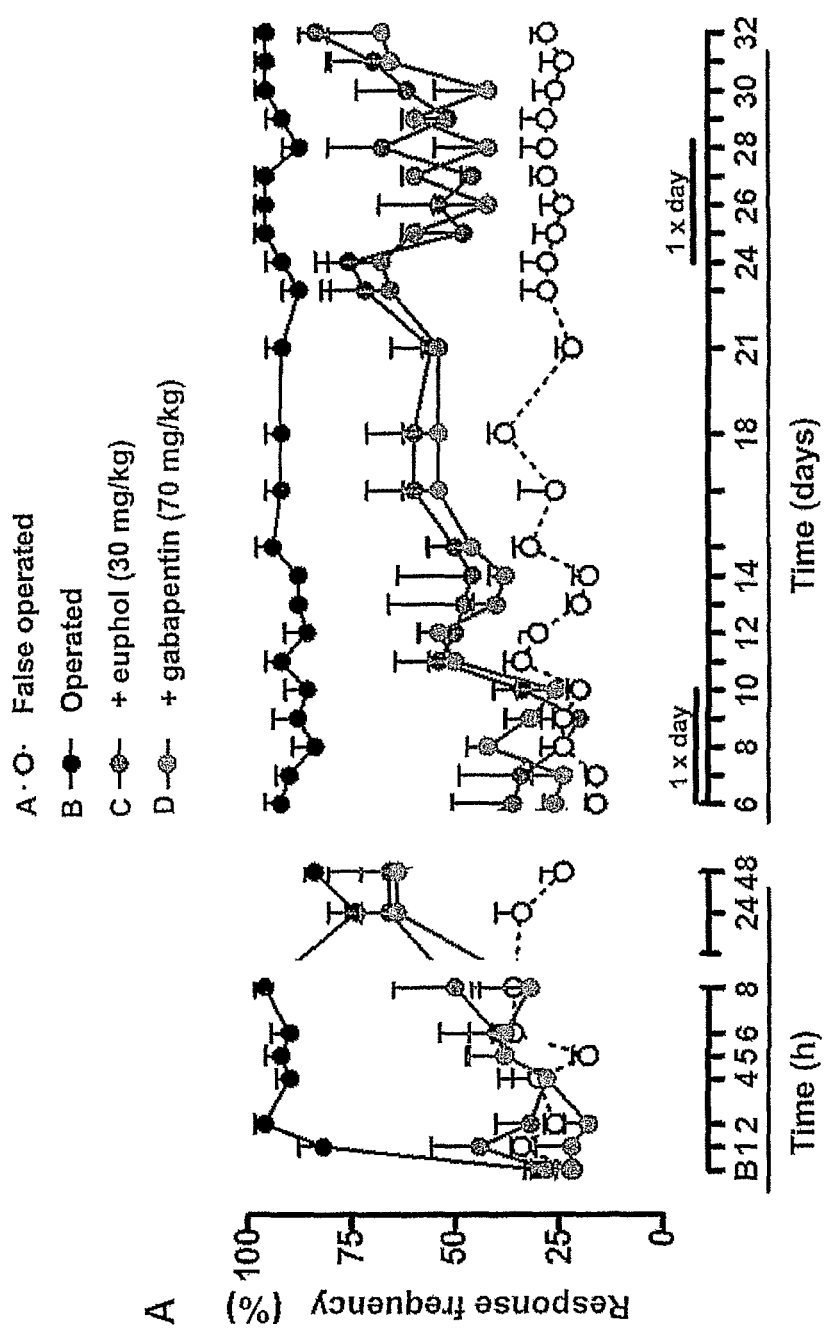
FIGS. 5A, 5B and 5C, 5A being a graph of time vs. frequency of response, and 5B and 5C the expression of the area under the curves of 4A for each tested compound, allowing a percentage comparison among them.
Figure 5B:
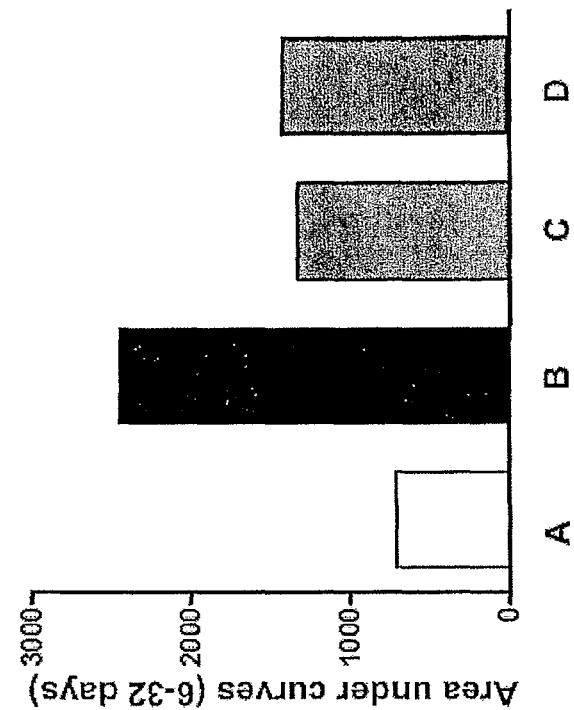
Figure 5C:
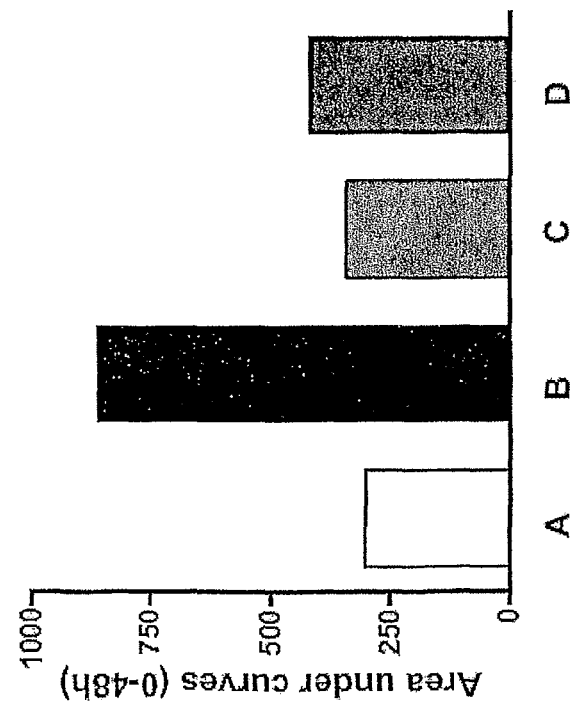

The results can be seen on FIGS. 5A, 5B and 5C, 5A being a graph of time vs. frequency of response, and 5B and 5C the expression of the area under the curves of 4A for each tested compound, allowing a percentage comparison among them.

As can be seen in FIGS. 5A and 5B, the acute treatment with euphol or gabapentin inhibited in a significant manner the mechanical nociceptive response induced by the partial constriction of the sciatic nerve.

Likewise, the prolonged treatment with euphol or gabapentin, once a day, reduced in a significant manner the mechanical hypernociception induced by the partial constriction of the sciatic nerve, with return to the nociceptive responses on the $10^{th}$ day of treatment.

With the help of the teachings and examples presented herein, a person skilled in the art is able to reproduce the invention in equivalent ways, using the same functions to obtain similar results, without departing from the scope of the invention defined in the attached claims.

The invention claimed is:

1. A method of treating neuropathic pain comprising administering to a mammal in need thereof a pharmacologically effective amount of euphol.

2. The method of claim 1, comprising administering a pharmacologically effective amount of euphol in a pharmacologically acceptable carrier or excipient.

3. The method of claim 1, comprising administering a pharmacologically effective amount of euphol combined with a pharmacologically effective amount of one or more second active agents.

4. The method of claim 3, wherein said one or more second active agents are antibiotics.

* * * * *